United States Patent
Gupta et al.

(10) Patent No.: US 10,466,153 B2
(45) Date of Patent: Nov. 5, 2019

(54) COREFLOOD TESTING SYSTEM AND METHODS FOR SIMULTANEOUS MEASUREMENT OF KEY CORE PROPERTIES

(71) Applicants: Robin Gupta, Spring, TX (US); Robert Longoria, Houston, TX (US); Jeffrey D. Spitzenberger, Richmond, TX (US); David C. Laverick, Spring, TX (US); Christopher A. Crowell, Spring, TX (US)

(72) Inventors: Robin Gupta, Spring, TX (US); Robert Longoria, Houston, TX (US); Jeffrey D. Spitzenberger, Richmond, TX (US); David C. Laverick, Spring, TX (US); Christopher A. Crowell, Spring, TX (US)

(73) Assignee: ExxonMobil Upstream Research Company, Spring, TX (US)

(*) Notice: Subject to any disclaimer, the term of this patent is extended or adjusted under 35 U.S.C. 154(b) by 191 days.

(21) Appl. No.: 15/429,926

(22) Filed: Feb. 10, 2017

(65) Prior Publication Data
US 2017/0248506 A1    Aug. 31, 2017

Related U.S. Application Data

(60) Provisional application No. 62/299,896, filed on Feb. 25, 2016.

(51) Int. Cl.
*G01N 15/08* (2006.01)
*G01N 13/00* (2006.01)
*E21B 49/02* (2006.01)

(52) U.S. Cl.
CPC ......... *G01N 15/0826* (2013.01); *E21B 49/02* (2013.01); *G01N 13/00* (2013.01)

(58) Field of Classification Search
CPC .................................................. G01N 15/0806
See application file for complete search history.

(56) References Cited

U.S. PATENT DOCUMENTS 2,345,935 A * 4/1944 Hassler .............. G01N 15/0826
73/38
2,618,151 A * 11/1952 Leas .................. G01N 15/0826
73/38

(Continued)

OTHER PUBLICATIONS

Braun, E.M. et al. (1981) "A Steady-State Technique for Measuring Oil-Water Relative Permeability Curves at Reservoir Conditions" *Society of Petroleum Engineers 10155*, SPE Annual Technical Conference and Exhibition, Oct. 4-7, San Antonio, Texas; pp. 1-10.

(Continued)

*Primary Examiner* — John Fitzgerald
*Assistant Examiner* — Alexander A Mercado
(74) *Attorney, Agent, or Firm* — ExxonMobil Upstream Research Company—Law Department

(57) ABSTRACT

Herein disclosed are apparatuses and methods related to coreflood testing apparatuses and methods for determining key physical properties of core specimens. More particularly, disclosed herein are coreflood inlet end-piece designs, coreflood testing systems and coreflood testing methods to enable simultaneous testing to obtain necessary data for determination for determining key physical properties of core specimens, which include the relative permeability and the capillary pressure, as well as, optionally the wettability of the core sample.

3 Claims, 8 Drawing Sheets

(56) References Cited

U.S. PATENT DOCUMENTS

| | | | | |
|---|---|---|---|---|
| 2,646,678 A | * | 7/1953 | Standing | B01D 29/111 210/212 |
| 2,705,418 A | * | 4/1955 | Francis | G01N 15/0826 73/38 |
| 2,821,680 A | * | 1/1958 | Slusser | G01N 15/0806 324/376 |
| 3,018,660 A | * | 1/1962 | Schmid | G01N 15/082 73/152.09 |
| 3,023,606 A | * | 3/1962 | Sarem | G01N 15/082 73/38 |
| 3,066,524 A | * | 12/1962 | Overhuls | G01N 15/0806 73/38 |
| 3,139,747 A | * | 7/1964 | Ferrell | G01N 15/0806 137/565.33 |
| 3,636,751 A | * | 1/1972 | Pasini, III | G01N 15/082 73/38 |
| 4,561,289 A | * | 12/1985 | Jones | G01N 15/0806 73/38 |
| 4,573,342 A | * | 3/1986 | Jones | G01N 15/08 73/38 |
| 4,587,857 A | * | 5/1986 | Bush | G01N 33/24 175/226 |
| 4,622,643 A | | 11/1986 | Dotson | |
| 4,638,447 A | | 1/1987 | Odeh | |
| 4,643,019 A | * | 2/1987 | Jones | G01N 15/0806 73/38 |
| 4,649,737 A | * | 3/1987 | Jones | G01N 15/08 73/38 |
| 4,663,711 A | | 5/1987 | Vinegar et al. | |
| 4,753,107 A | * | 6/1988 | Reed | G01N 15/0806 73/38 |
| 4,860,582 A | * | 8/1989 | Bourguet | E21B 49/005 73/152.07 |
| 4,864,846 A | * | 9/1989 | Jones | G01N 15/0806 73/38 |
| 4,868,751 A | | 9/1989 | Dogru et al. | |
| 4,893,504 A | | 1/1990 | O'Meara, Jr. et al. | |
| 5,042,580 A | | 8/1991 | Cullick et al. | |
| 5,086,643 A | | 2/1992 | Marek | |
| 5,167,139 A | * | 12/1992 | Lafargue | G01N 15/082 73/38 |
| 5,245,859 A | | 9/1993 | Smith et al. | |
| 5,263,360 A | * | 11/1993 | Blauch | C09K 8/58 166/250.02 |
| 5,297,420 A | | 3/1994 | Gilliland et al. | |
| 5,341,101 A | * | 8/1994 | Maerefat | G01N 15/08 250/255 |
| 5,363,692 A | * | 11/1994 | Lafargue | G01N 33/241 73/38 |
| 5,493,226 A | * | 2/1996 | Honarpour | E21B 49/005 324/376 |
| 5,563,333 A | * | 10/1996 | Haines | G01N 15/0806 73/38 |
| 6,450,012 B1 | * | 9/2002 | Mayer | G01M 3/227 73/40.7 |
| 6,655,192 B2 | * | 12/2003 | Chavdar | G01N 15/0826 73/37 |
| 8,683,858 B2 | | 4/2014 | Piri | |
| 8,863,567 B2 | * | 10/2014 | Jappy | E21B 21/003 73/61.64 |
| 10,133,832 B2 | * | 11/2018 | Burghardt | G06F 17/5009 |
| 2006/0116828 A1 | | 6/2006 | Chen et al. | |
| 2011/0306525 A1 | | 12/2011 | Lighthelm | |
| 2013/0196886 A1 | | 8/2013 | Barnes et al. | |
| 2013/0276554 A1 | * | 10/2013 | Matthews | E21B 25/005 73/864 |
| 2015/0219789 A1 | * | 8/2015 | Pairoys | G01V 9/00 73/118.04 |
| 2018/0335374 A1 | * | 11/2018 | Kanj | G01N 15/0826 |
| 2019/0025169 A1 | * | 1/2019 | Zhang | F17C 13/002 |

OTHER PUBLICATIONS

Ebeltoft, E., et al. (1996) "A Novel Experimental Apparatus for Determination of Three-Phase Relative Permeabilities at Reservoir Conditions" *SCA Conference Paper Number 9636*, pp. 1-9.

Gupta, R. et al., "Intercept Method—A Novel Technique to Correct Steady-State Relative Permeability Data for Capillary End-Effects," SPE 171797-MS, Abu Dhabi Int'l. Petroleum Ex. & Conf., Abu Dhabi, UAE, 28 pgs. (Nov. 10-13, 2014).

Jennings, Jr., J.W. et al., "Simultaneous Determination of Capillary Pressure and Relative Permeability by Automatic History Matching," SPE 14418, *SPE Formation Evaluation*, pp. 322-328(Jun. 1988).

Kokkedee, J.A., "Simultaneous Determination of Capillary Pressure and Relative Permeability of a Displaced Phase," SPE 28827, European Petroleum Conf., London, U.K., 10 pgs. (Oct. 25-27, 1994).

Longren, D. et al., "Water-Oil Capillary Pressure and Wettability Measurements Using Micropore Membrane Technique" SPE 30006, Int'l. Meeting on Petroleum Engineering, Beijing, PR China, pp. 543-553 (Nov. 14-17, 1995).

Pini, R. et al., "Simultaneous Determination of Capillary Pressure and Relative Permeability Curves from Core-Flooding Experiments with Various Fluid Pairs," *Water Resources Research*, vol. 49, pp. 3516-3530 (2013).

Richardson, J.G. et al., "Laboratory Determination of Relative Permeability," SPE 952187, *Petroleum Transactions, AIM*, vol. 195, pp. 187-197 (1952).

Virnovsky, G.A., et al., "Relative Permeability and Capillary Pressure Concurrently Determined from Steady—State Flow Experiments," 8$^{th}$ European IOR-Symposium, Vienna, Austria. 10 pgs. (May 15-17, 1995).

* cited by examiner

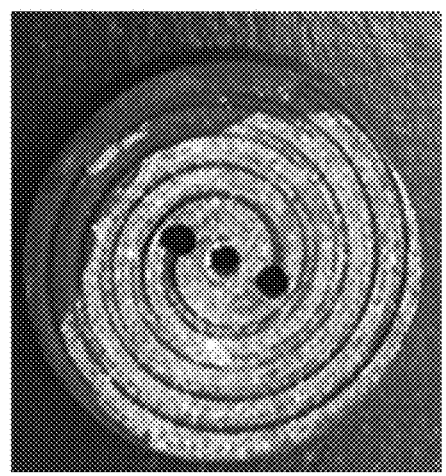
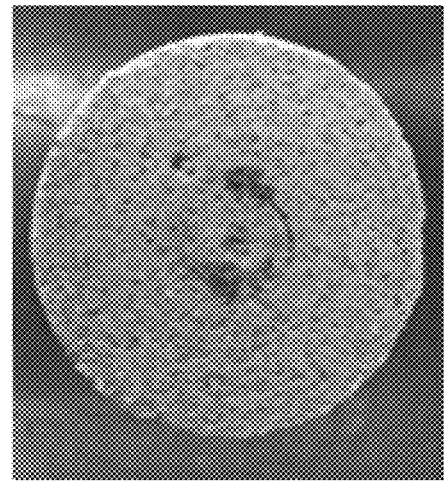
*FIG. 6A*  *FIG. 6B*
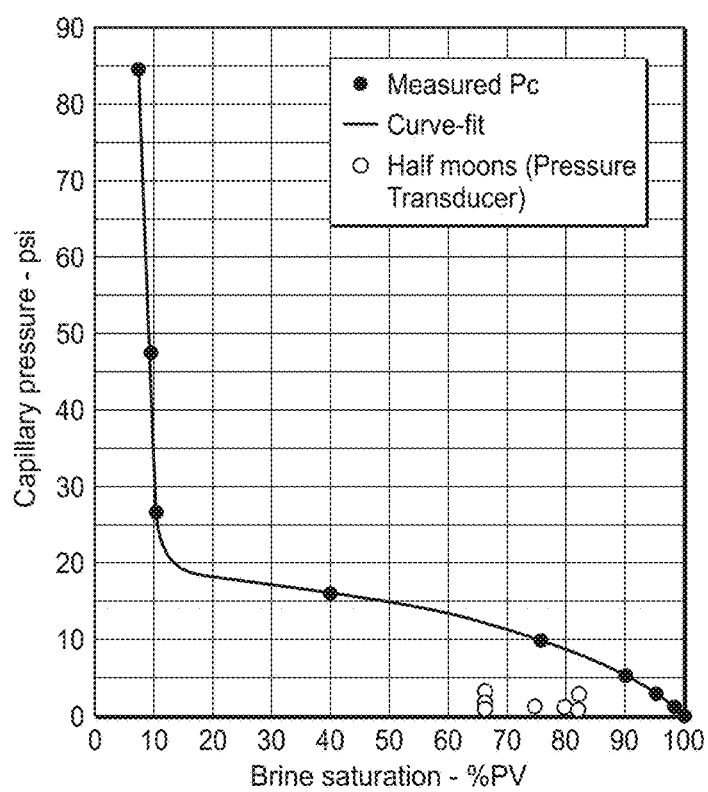
*FIG. 7*

COREFLOOD TESTING SYSTEM AND METHODS FOR SIMULTANEOUS MEASUREMENT OF KEY CORE PROPERTIES

CROSS-REFERENCE TO RELATED APPLICATION

This application claims the benefit of U.S. Provisional Patent Application 62/299,896 filed Feb. 25, 2016 entitled COREFLOOD TESTING SYSTEM AND METHODS FOR SIMULTANEOUS MEASUREMENT OF KEY CORE PROPERTIES, the entirety of which is incorporated by reference herein.

FIELD

Herein disclosed are apparatuses and methods related to coreflood testing apparatuses and methods for determining key physical properties of core specimens.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

In the oil reservoir discovery and drilling industry, a critical aspect of determining where to drill wells, what type of wells to drill, managing production in existing wells, and determining the type of oil extraction methods, injection fluids, and operating conditions to utilize in a well, is in determining key physical properties of the underground area or well media. This is typically done in the industry by removing several core samples from identified underground structures or in a specific well in question and testing the core(s) or core samples for several key physical aspects. Utilizing several of these core properties, engineers and geologists can use experience, further testing, and/or models to best select where to drill wells, which type of wells to drill, what extraction methods to use in each well, extraction fluids to utilize, as well as the optimum extraction conditions to achieve maximum cost efficiency and production from a given well configuration or oil reservoir.

Three key core physical properties that may be obtained from a core sample are relative permeability, capillary pressure, and wettability. The problem in the industry is that the simple, direct, and most reliable/repeatable conventional methods in the industry require at least three separate tests to be run on a core sample to obtain each of these three core properties. Additionally making conventional techniques problematic is that these measurements cannot always be made on the same core sample and using same lab conditions (e.g., pressure, temperature and fluids). A sample used in one test to determine one of these key physical properties most often is not used in the next separate test for another of these key properties. This not only leads to additional costs and time, but may lead to correlation errors on these properties since even though the core samples may be obtained from the same general underground area or well, like fingerprints, no two core samples are exactly alike. Hence, technical issues occur such as mismatched data sets; anomalies from using different samples, test conditions, and fluids in the various tests; propagation of errors from combining results from different tests; and gaps in data sets over saturation ranges.

One of the commonly used standard tests in the industry is called a "coreflood" test. However, with conventional coreflood testing, only one of the three key properties of the core, relative permeability, is commonly measured.

Lab tests performed to obtain key rock-fluid properties often involve injecting fluids into a rock sample, also called a "core", a "core plug" or "core sample". One such lab technique utilized in the industry is commonly referred to as a "steady-state coreflood". In a typical steady-state coreflood test, two different fluids are co-injected in a core plug (or core plugs stacked in series) until a steady-state condition or close to steady-state condition is obtained. The core(s) are placed between inlet and outlet end pieces during a coreflood test. The pressure in phases at the inlet and outlet of the core are often used as inputs to infer key reservoir properties, e.g., relative permeability ($k_r$). The difference in phase pressure for the two fluids is close to zero at the outlet of the core because of the phenomenon called "Capillary End-Effect" ("CEE"); however, this difference in phase pressure is non-zero at the core inlet. In conventional coreflood testing apparatus designs, the separate phase pressures cannot be individually measured due to phase mixing at the inlet-end piece of the apparatus; hence the difference in the phase pressures at the inlet are generally assumed to be zero.

Capillary pressure ($P_c$) is another key rock-fluid property that is often measured in the lab. Relative permeability and capillary pressure serve as key inputs in reservoir simulation to understand flow through porous media in hydrocarbon reservoirs. Capillary pressure cannot be measured in a conventional coreflood test. Separate testing, typically with other samples than those used in the coreflood tests, must be used to measure the capillary pressure of the core sample. Common capillary pressure measurement lab techniques are centrifuge method and porous plate method, while common relative permeability measurement techniques are steady-state or unsteady state corefloods. In current practice, two separate experiments are performed on different cores to measure capillary pressure and relative permeability for a given hydrocarbon reservoir facies, which can add challenges to test interpretation. If the geological characterization of a core is erroneous, then current approach may risk misinterpretation of both these measured reservoir properties for a given reservoir facies. Additionally, often due to limitation of capillary pressure lab equipment, both capillary pressure and relative permeability measurements are often performed at different test conditions, e.g., test temperature, pore pressure, net confining stress, fluid properties, etc. However, these lab measurements could be sensitive to test conditions. It is always preferred to perform both capillary pressure and relative permeability tests at identical conditions and, if it would be possible, with the same core sample. A capillary pressure curve for a core can have both positive and negative values with fluid saturation. The positive or negative part of the capillary pressure could be called forced or spontaneous depending on the test fluids and measurement modes: imbibition or drainage. In other words, a capillary pressure curve that crosses zero pressure mark has both spontaneous and forced portions. Existing methods, like centrifuge, have limitations that they can only measure one side (either positive or negative) of a capillary pressure curve, which is also referred as forced imbibition or forced drainage part of a capillary pressure curve. It is preferred to capture full characteristic of a capillary pressure, both forced and spontaneous portions, for better depletion planning and performance prediction for a hydrocarbon reservoir.

The third key core physical property, wettability, also requires separate testing from the conventional coreflood test, as well as the separate tests described above that are required to determine the capillary pressure. Conventional testing to determine the wettability of a core sample are Amott-Harvey or USBM (U.S. Bureau of Mines) method. This method requires performing a combination of spontaneous imbibition (imbibing a core sample in a fluid) and centrifuge test for both imbibition and drainage cycles (definition discussed later)

Much of the previous work, such as Longren (see Longeron, D., Hammervold, W. L., & Skjaeveland, S. M., Jan. 1, 1995, "Water-Oil Capillary Pressure and Wettability Measurements Using Micropore Membrane Technique", Society of Petroleum Engineers, doi:10.2118/30006-M), Richardson (see Richardson, J. G., Kerver, J. K., Hafford, J. A., & Osoba, J. S., Aug. 1, 1952, "Laboratory Determination of Relative Permeability", Society of Petroleum Engineers, doi:10.2118/952187-G); Jennings (see Jennings, J. W., McGregor, D. S., & Morse, R. A., Jun. 1, 1988, "Simultaneous Determination of Capillary Pressure and Relative Permeability by Automatic History Matching", Society of Petroleum Engineers. doi:10.2118/14418-PA); and Virnovsky (see Virnovsky, G. A., Guo, Y., & Skaeveland, S. M., May 15, 1995, "Relative Permeability and Capillary Pressure Concurrently Determined from Steady-State Flow Experiments", 8th. European IOR-Symposium in Vienna, Austria) related to isolating injection phases at coreflood inlet had been performed or proposed using porous plate or membranes. In these techniques, surface chemical property (wettability preference) of porous plate or membrane only allows one phase to pass through it and repels the other phase. Drawbacks of with the use of porous plates or membranes are that it is difficult to maintain wettability for long time for certain phases, and the initial wettability can alter to different wetting condition during the course of a test. Further, many of these designs are aimed to improve the porous plate technique of capillary pressure measurement, which utilizes using a fixed wettability membrane at the outlet to only allow one phase to flow out, and are not designed for conventional coreflood tests.

Richardson (see Richardson, J. G., Kerver, J. K., Hafford, J. A., & Osoba, J. S., Aug. 1, 1952, "Laboratory Determination of Relative Permeability", Society of Petroleum Engineers, doi:10.2118/952187-G), and Gupta (see Gupta, R., & Maloney, D. R. Nov. 10, 2014, "Intercept Method—A Novel Technique to Correct Steady-State Relative Permeability Data for Capillary End-Effects", Society of Petroleum Engineers. doi:10.2118/171797-MS) suggested that the pressure difference between the wetting and non-wetting fluid is a measure of the capillary pressure of the sample at the inflow end. However, they did not account for the need to subtract viscous pressures contribution from inlet phase pressure difference, which this invention addresses and lays out as part of the method. They also did not provide an inlet end piece design to measure inlet phase pressure. Richardson also stated that the difference of wetting and non-wetting phase pressure at any point in porous media is equal to the capillary pressure corresponding to the saturation at the point. They demonstrated the concept by cementing wetting phase (oil) pressure probes made of ceramic porous media to core walls and gas (non-wetting) pressure probes to the rubber sleeve. Their experiments showed that the pressure difference between the wetting and non-wetting fluid inside the core is constant away from the outlet end and equals to capillary pressure. However, cementing a probe on the core is not a preferred method because it might damage the core or alter the wettability of the native-condition core. Further, cementing probes for each test could be time intensive and susceptible to leaks.

Kokkedee (see Kokkedee, J. A., Jan. 1, 1994, "Simultaneous Determination of Capillary Pressure and Relative Permeability of a Displaced Phase. Society of Petroleum Engineers", doi:10.2118/28827-MS) and Pini (see Pini, Ronny, and Sally M Benson, 2013, "Simultaneous Determination of Capillary Pressure and Relative Permeability Curves from Core-Flooding Experiments with Various Fluid Pairs", Water Resources Research 49 (6): 3516-30, doi: 10.1002/wrcr.20274) proposed that capillary pressure is equal to pressure drop across the core at low rates. No special end piece is utilized in this technique and this technique relies on the assumption that viscous forces are small compared to capillary forces, which is not true in many test conditions and can thus result in inaccurate results for a corefloods capillary pressure measurement.

This problem has been recognized in the industry for many years. For instance, U.S. Pat. No. 4,893,504 to O'Meara Jr. et al. (patent issued Jan. 16, 1990) attempted to devise an integrated test to solve this problem known and faced in the industry. However, O'Meara requires special and complex imaging techniques (such as X-ray CT or Nuclear Magnetic Resonance Imaging, NMRI) and employs saturation profile images of fluids in a porous sample in order to determine the relative permeability and capillary pressure of the sample. Not only do the techniques of O'Meara require expensive and require complex data collection equipment, they also require complex, and what may be somewhat subjective, analysis techniques that are not confirmed with standard industry test methods.

This problem has been recognized in the industry for many years. For instance, U.S. Pat. No. 5,493,226 to Honarpour et al. (patent issued Feb. 20, 1996) describes a method for testing a core sample to obtain at least two of these key core properties, relative permeability and capillary pressure (resistivity of the core sample, which is also measured in the Honarpour method, is an electrical property and is generally not considered as a key core property for conventional oil drilling and production). However, as can be seen, the Honarpour apparatus and test method is extremely complicated as compared to a conventional core flood test (as is described in the Description section of the present disclosure). The Honarpour method requires a very complicated apparatus, including pump controllers, multiple positive displacement cylinders placed along the length of the core sample, fluid phase-specific porous membrane, as well as a microwave generation system and detector. None of the elements are part of a conventional coreflood test apparatus.

Honarpour does however point to the problem in the art as discussed above as he notes "Further, as will be understood by those skilled in this art, relative permeability and capillary pressure are interrelated and should be measured simultaneously. However, these properties are commonly obtained from different measurements using different methods, fluids, and testing conditions on different core samples from the same reservoir. As can be imagined, this results in inconsistencies between the collected data." (see Honarpour at column 3, lines 12-19). To our knowledge, all three (3) of these properties cannot be determined by a single coreflood test as currently utilized in the industry.

As can be seen, there is a need by practitioners of the art for a simple, accurate and effective method without the need for such apparatus as porous plates, membranes, costly x-ray or NMRI apparatus and analysis techniques (which can only provide for an "indirect measurement" of many of the coreflood properties), as well as a method with the ability to measure relative permeability, capillary pressure, and optionally, wettability utilizing a single coreflood sample. Additionally, the ability to combine relative permeability, capillary pressure and wettability tests into a single testing system and test method results in significant reduction in experimental time and effort compared to each test performed separately along with addressing the existing problems in the industry as discussed above.

SUMMARY

In an embodiment herein is an inlet end-piece for a coreflood testing system, comprising:
a first surface;
a first phase inlet port substantially located at the first surface; and
a second phase inlet port substantially located at the first surface;
wherein substantially within the plane of the first surface, the first phase inlet port and the second phase inlet port are separated by at least one isolation member.

In another embodiment herein is a coreflood testing system comprising:
a coreholder which comprises:
a cavity;
a core sample placed with the cavity;
an inlet end-piece at a first end of the cavity; and
an outlet end-piece at a second end of the cavity, wherein the second end of the cavity is opposite of the first end of the cavity;
wherein the inlet end-piece comprises:
a first surface;
a first phase inlet port substantially located at the first surface; and
a second phase inlet port substantially located at the first surface;
wherein substantially within the plane of the first surface, the first phase inlet port and the second phase inlet port are separated by at least one isolation member; and
wherein the isolation member is in contact with the first surface and a first end of the core sample, and creates a seal that fluidly isolates the first phase inlet port from the second phase inlet port substantially within the plane of the first surface.

In another embodiment herein is a coreflood testing process, comprising:
flowing a first phase fluid through a first phase fluid inlet of an inlet end-piece of a coreholder and into a first inlet face of a core sample, wherein the core sample is located within a cavity of the coreholder; and
flowing a second phase fluid through a second phase fluid inlet of the inlet end-piece to the coreholder and into the first inlet face of the core sample;
wherein substantially with in the plane of the first inlet face of the core sample, the first phase fluid is fluidly isolated from the second phase fluid by at least one isolation member.

BRIEF DESCRIPTION OF THE DRAWINGS

The advantages of the present techniques are better understood by referring to the following detailed description and the attached drawings, in which.

FIGS. 6A and 6B shows the post-test pictures of a coreflood inlet end-piece (FIG. 6A) and the inlet face of the core sample (FIG. 6B).
FIG. 7 shows the difference of phase pressures at steady-state condition for multiple fraction flow and multiple rates at each fractional flow utilizing the "half-moons" coreflood inlet end-piece (as illustrated in FIG. 2D)

DETAILED DESCRIPTION OF THE EMBODIMENTS

Figure 1A:
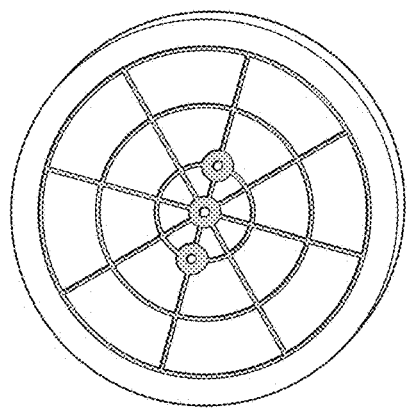
FIGS. 1A through 1C illustrate some examples of coreflood inlet end-pieces utilized in the industry.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

Capillary end-effect—A phenomenon in flow through porous media that results in capillary pressure equal to zero near core plug outlet, which causes accumulation one phase near the outlet. The effect can reflect as experimental artifacts in phase saturation and pressure drop measurements.

Capillary pressure ($P_c$)—The difference of non-wetting to wetting phase pressure. However, for simplification, water is considered most wetting and gas is considered most non-wetting among water, oil and gas. Therefore, capillary pressure is often reported as oil-water, gas-water or gas-oil phase pressure difference. This is typically measured in units of pressure (e.g., psi)

Composite—Series of core plugs stacked together in series

Core or core plug—Referred to a piece of subterranean rock cut often in cylinder shape. A core plug for a hydrocarbon bearing subterranean rock is a few centimeters in diameter and length Coreflood—A lab method that involves injecting fluids through a porous media (such as a Core) and measuring the properties of physical media.

Drainage—Injection of non-wetting phase in a core, or increasing non-wetting phase saturation in a core.

Imbibition—Injection of wetting phase in a core, or increasing wetting phase saturation in a core.

The Intercept Method—A method to correct capillary end-effect artifact from a steady-state coreflood test (see Gupta, R., & Maloney, D. R. Nov. 10, 2014, "Intercept Method—A Novel Technique to Correct Steady-State Relative Permeability Data for Capillary End-Effects", Society of Petroleum Engineers. doi:10.2118/171797-MS).

Net Confining Stress—The difference of overburden pressure and pore pressure. This is typically measured in units of pressure (e.g., psi).

Overburden Pressure—The pressure maintained around a coreflood core to replicate hydrocarbon reservoir condition. This pressure is larger than pore pressure. This is typically measured in units of pressure (e.g., psi).

Pore pressure—The pressure in the rock during a coreflood test. A device called back pressure regulator (BPR) is routinely used to fix a desired pore pressure at the outlet end of core in a coreflood test. This is typically measured in units of pressure (e.g., psi).

Relative Permeability ($k_r$)—Relative permeability is the ratio of effective permeability of a particular fluid at a particular saturation to a reference permeability. Relative permeability quantifies the reduction in flow capability due to the presence of multiple mobile fluids in a porous media.

Steady-state coreflood—A laboratory method where two or more phases are injected in in a porous media (often core plug or plugs stacked in series) until a steady-state or close to steady state condition is obtained. The steady-state pressure and saturation data is used to measure rock properties.

Unsteady-state coreflood—A laboratory method where a phase in injected in a porous media (often core plug or plugs stacked in series), and dynamic pressure and saturation data is used to measure rock properties.

Wettability—Tendency of one fluid to adhere or spread on a rock surface relative to another fluid. This is a dimension less number. It is commonly measured using Amott-Harvey (or Amott) or USBM (US Bureau of Mines).

Wetting phase—Phase which has higher tendency to adhere on a surface compared to the other phase. The other phase is called non-wetting. Gas is non-wetting relative to oil and water.

A "hydrocarbon" is an organic compound that primarily includes the elements hydrogen and carbon, although nitrogen, sulfur, oxygen, metals, or any number of other elements may be present in small amounts. As used herein, hydrocarbons generally refer to components found in crude oil, condensates, natural gas or hydrocarbon gas.

"Pressure" is the force exerted per unit area by the gas on the walls of the volume. Pressure can be shown as pounds per square inch (psi). "Atmospheric pressure" refers to the local pressure of the air. "Absolute pressure" (psia) refers to the sum of the atmospheric pressure (14.7 psia at standard conditions) plus the gauge pressure (psig). "Gauge pressure" (psig) refers to the pressure measured by a gauge, which indicates only the pressure exceeding the local atmospheric pressure (i.e., a gauge pressure of 0 psig corresponds to an absolute pressure of 14.7 psia). The term "vapor pressure" has the usual thermodynamic meaning.

"Single Coreflood Test" as used herein means a coreflood test or series of coreflood tests performed at multiple conditions on a single core sample within a single coreflood system. Multiple conditions can be variations of one or many variables like flow rates, fraction flow rates, temperature or pressure.

"Substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

In embodiments of the present invention, are devices, systems and methods that provide the ability to measure injection phase pressures at the core inlet therefore enabling the calculation of the capillary pressure of the core after appropriate correction of the data for the viscous effects which technique is further disclosed herein. Thus, the present invention can enable measuring both relative permeability and capillary pressures on the same core (or cores stacked in series) at the same test condition in the same test. If both imbibition and drainage cycles are performed in the test, then capillary pressures for both injection cycles can be obtained. Wettability, another important petrophysical property, can be calculated if both imbibition and drainage capillary pressure cycles are available using established methods like Amott and USBM (US Bureau of Mines) wettability index method. Combining relative permeability, capillary pressure and wettability tests into one test results in significant reduction in experimental time and effort compared to performing each test separately along with addressing the problems discussed above.

One embodiment of the present invention is the use of a novel coreflood testing end-piece design. As noted prior, a coreflood test typically involves the injection of two (2) phases (i.e., input fluids) into coreflood testing system (or "coreflood system" herein). However, the systems and methods as taught and disclosed herein are not limited to two-fluid-phase systems, and can also be used with coreflood systems with three (3) or more phases (i.e., inlet fluids). However, for the sake of simplicity in describing the embodiments here, the invention(s) herein will be described in the embodiments of a two (2) phase coreflood system. Typical two (2) phase coreflood systems of importance to the industry would generally consist of the following: oil/water, oil/gas, and gas/water, wherein the term "water" as used herein in this context can be water, a brine solution, or a water solution with chemical additives. As noted above, a three (3) phase could exemplarily consist of the following: oil/water/gas, oil/water/chemical, oil 1/oil 2/water, oil 1/oil 2/gas, oil/gas1/gas2, or other similar combinations, wherein the term water as used herein in this context can be water, a brine solution, or a water solution with chemical additives.

Therefore, it is noted herein that while the coreflood inlet end-pieces, apparatuses, systems and process concepts disclosed herein are typically explained and exemplified herein with a two-fluid coreflood system, that these concepts can be expanded to coreflood inlet end-pieces, apparatuses, systems and processes for three-fluid systems as well. Unless otherwise specified herein, the term "fluid" or "fluids" as utilized can mean either a liquid or gas.

Figure 1B:
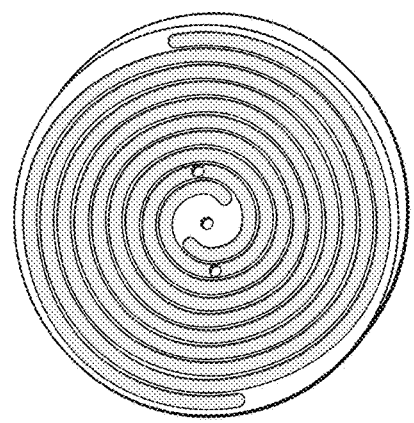
Figure 1C:
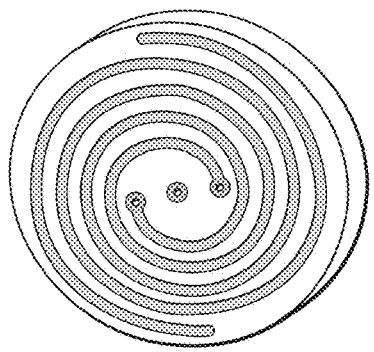

FIGS. 1A through 1C illustrate some examples of coreflood inlet end-pieces utilized in the industry. FIG. 1A illustrates a "cross" design pattern, FIG. 1B illustrates a "spiral" pattern, and FIG. 1C illustrates a "modified spiral". These end-pieces are designed to improve the mixing of the two phases as well as the distribution of the phases across the inlet phase of the core sample. However, as has been noted, these systems do not, nor attempt to isolate the two inlet phases at the face of the core sample. In standard industry coreflood systems, these coreflood inlet end-pieces are often utilized with a screen between the coreflood inlet end-pieces and the core sample to not only prevent particulate matter from entering the core sample, but also to improve the mixing of the two inlet phases. In the prior art, no attempt is made to isolate the two phases at the core inlet and in fact, items, such as the inlet screen as mentioned, help to promote mixing (and thus non-isolation) of the two inlet phases. With these conventional coreflood inlet end-pieces, as discussed, the coreflood testing system can only be utilized to measure relative permeability ($k_r$) of the fluids; capillary pressure ($P_c$) and wettability cannot be measured utilizing these coreflood testing system designs.

In the present embodiments is included a novel coreflood inlet end-piece design wherein two (2) phase inlet ports (a first phase inlet port and a second phase inlet port) are separated by at least one isolation member. In a more preferred embodiment, is a coreflood inlet end-piece which further includes a core inlet pressure port wherein the first phase inlet port, the second phase inlet port and the core inlet pressure port are all separated by at least one isolation member.

Figure 2A:
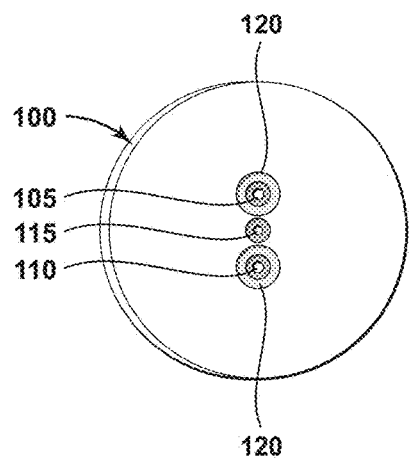
FIGS. 2A through 2D illustrate some examples of the novel coreflood inlet end-pieces herein.

Representative designs that were manufactured and tested herein are shown in FIGS. 2A through 2D. These designs are only representative and the embodiments disclosed herein are not limited to the four (4) examples shown in FIGS. 2A through 2D. FIG. 2A illustrates an o-ring design coreflood inlet end-piece (100) wherein a first phase inlet port (105), a second phase inlet port (110) and a core pressure port (115) are all separated by the use of two o-rings (120), wherein the two o-rings are situated around each the first phase inlet port (105), a second phase inlet port (110) and provides isolation of a first phase inlet port (105), a second phase inlet port (110) and a core inlet pressure port (115) at the coreflood inlet face.

Figure 2B:
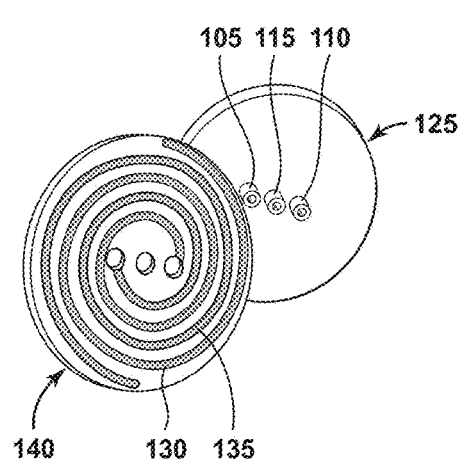
Figure 2C:
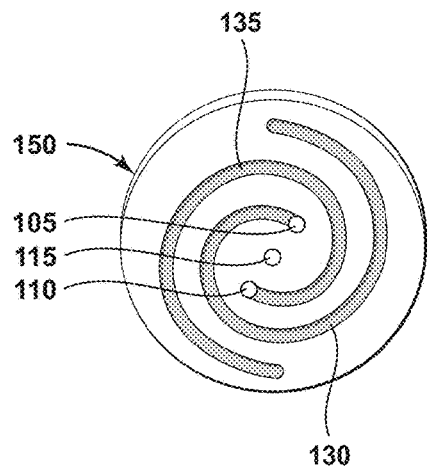
Figure 2D:
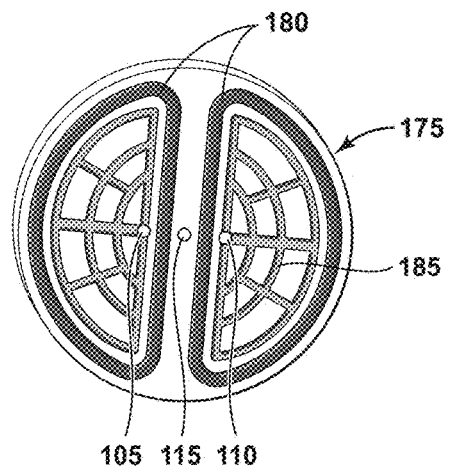

FIG. 2B illustrates another embodiment of the coreflood inlet end-piece utilizing an "elastomer spiral face" coreflood inlet end-piece (125) wherein the sealing areas for a first phase inlet port (105), a second phase inlet port (110), and the core inlet pressure port (115) and port channels (130 & 135) are fabricated into the elastomer face (140) and the three inlet ports (105, 110 and 115) are separated by at least one isolation member, i.e., the elastomer end-piece (140). FIG. 2C illustrates yet another embodiment of the coreflood inlet end-piece utilizing an "elastomer spiral gasket" coreflood inlet end-piece wherein first phase inlet port (105), a second phase inlet port (110), and the core inlet pressure port (115) and port channels (130 & 135) are fabricated by voids fabricated through the elastomer face gasket (155), wherein the void portions of the face gasket form the channels and the three inlet ports are separated at least one isolation member, the elastomer face gasket (155). FIG. 2D illustrates yet another embodiment of the coreflood inlet end-piece utilizing a "half-moon" coreflood inlet end-piece wherein a first phase inlet port (105), a second phase inlet port (110), and the core inlet pressure port (115) are separated by a "half-moon", or substantially semi-circular shaped gasket (180) that is situated around each a first phase inlet port (105), a second phase inlet port (110) and provides isolation of a first phase inlet port (105), a second phase inlet port (110) and a core inlet pressure port (115) at the coreflood inlet face. In preferred embodiments, the area within the boundaries of each of the gaskets (or isolation members) surrounding the first phase inlet port (105) and the second phase inlet port (110) are at least 25%, more preferably 30% and most preferably at least 35% of the total area of the surface of the face of the coreflood inlet end-piece (100). Optionally, in the design as shown in FIG. 2D, grooves (185) may be cut or machined into the face with the gasketed areas of a first phase inlet port (105), a second phase inlet port (110), or both in order to assist in distribution of the phase fluid(s) across the coreflood inlet face within each of the gasketed areas.

It should be noted here that the ports on the coreflood inlet end-piece are "substantially" located at the surface face of the coreflood inlet end-piece. This means that they can be either flush with the surface face of the coreflood inlet end-piece (as illustrated in FIGS. 2A, 2C and 2D), or slightly protrude from the surface face of the coreflood inlet end-piece (as illustrated in FIG. 2B) as long as such ports do not interfere with the sealing capability between the surface face of the coreflood inlet end-piece/isolation member and the inlet surface face of the core sample. Also, the term "substantially within the plane" of the surface face of the coreflood inlet end-piece as it relates to the separation of the first phase inlet port, the second phase inlet port, and/or the core inlet pressure port means that such separation can occur in a plane slightly recessed in the surface face of the coreflood inlet end-piece (such as illustrated in FIGS. 2A and 2D where isolation members/gaskets may sit in recesses in the surface face of the coreflood inlet end-piece), or at or above the face of the coreflood inlet end-piece (such as illustrated in FIGS. 2B and 2C where the isolation members/gaskets may sit on the surface face of the coreflood inlet end-piece).

Figure 3:
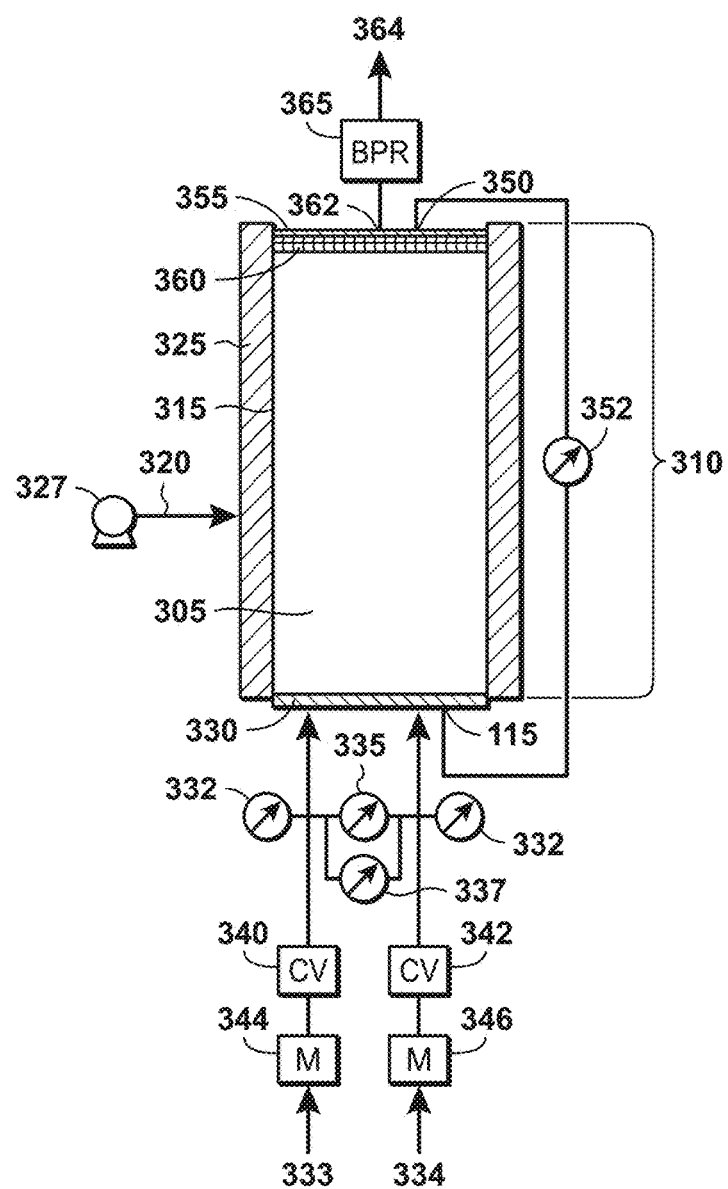
FIG. 3 illustrates an embodiment of a novel coreflood testing system disclosed herein utilizing the coreflood inlet end-pieces as described herein.

These novel coreflood inlet end-piece designs may be further utilized in a novel coreflood testing system. An embodiment of a coreflood testing system (300) utilizing the coreflood inlet end-pieces as previously described as well as additional systems and hardware system is shown in FIG. 3. Here the coreflood testing system has hardware that will take advantage of the additional information that is enabled by the coreflood inlet end-pieces as previously described in order to measure relative permeability and capillary pressure, as well as optionally, wettability from a single coreflood test utilizing a single core plug or single set of core plugs.

Here, a core sample (or series of core samples) to be tested (305) is placed in a core holder (310). Preferably, and as will be illustrated in the description herein, the core and the coreflood holder will be substantially cylindrical in shape, but the disclosure herein is not limited to such geometries or configurations. Optionally, an overburden sleeve (315) may be placed around the circumference of the core. This is preferably made of an elastomer material (such as rubber) that will conform to the core circumference and provide a fluid barrier between the core (305) and an overburden fluid (320) where overburden fluid can be pumped into a cavity (325) surrounding the overburden sleeve (315) by an overburden pump (327) to maintain a controllable net confining stress (difference on overburden and pore pressure) in the core holder (310). In the present invention, a coreflood inlet end-piece (330) of the present invention (such as exemplified in the non-limiting examples of FIGS. 2A through 2D herein), is installed at the inlet end of the core holder (310).

Because the first phase inlet port (105) and the second phase inlet port (110) are separated and pressure isolated by the configurations as exemplified in the coreflood inlet end-piece (330), the pressures in the first phase and the second phase fluids at the core face can be separately measured, pressure gauges (332) (or, generically, a pressure measurement device which would include pressure transmitters) can be installed on the inlet lines for each the first phase fluid stream (333) and the second phase fluid stream (334), preferably near the coreflood inlet end-piece (330) in order to obtain separate pressure for each phase fluid. A differential inlet pressure between the two phase fluids at the inlet can then be obtained. Preferably, either optionally or in addition to the individual pressure gauges (332), a differential pressure gauge (or gauges, generically, a differential pressure measurement device) is utilized to measure the differential inlet pressure between the two phase fluids at the inlet. However, the differential pressure across the core sample may be determined by any device or combination of devices suitable to directly measure and/or to calculate the differential pressure across the core sample (herein collectively referred to as a "differential measurement device"). It should be noted that the difference in phase pressures at the inlet can be positive or negative. Hence, the differential pressure transducers that can accurately capture both positive and negative values should be selected and calibrated accordingly. FIG. 3 shows a preferred embodiment wherein both a low-range differential inlet pressure gauge (335) and a high-range differential inlet pressure gauge (337) is utilized to improve accuracy of the data measurements over the full range of the coreflood testing.

This differential pressure measurement cannot be obtained with the coreflood inlet end-piece designs or the coreflood systems of the prior art. These measurements are required in order to be able to determine both the relative permeability and capillary pressure, as well as optionally, wettability from a single coreflood test utilizing a single core plug or multiple core plugs stacked in series in a simple and direct measurement system such as disclosed herein. As noted, in the prior art the relative permeability and capillary pressure cannot be measured in a single coreflood test without, as noted, the use of such complex equipment and analysis utilizing either X-ray or NMR technologies.

Continuing with FIG. 3, in preferred embodiments, a first phase check valve (340) and a second phase check valve (342) are installed in the inlet lines for each the first phase fluid stream (333) and the second phase fluid stream (334). It is recommended to have these check values behind the pressure gauges at the inlet to prevent back flow, which could result in phase mixing and pressure equilibration of injection phases. In preferred embodiments, a first phase flow meter (344) is utilized to measure the first phase fluid flow rate and a second phase flow meter (346) is utilized to measure the second phase fluid flow rate. In preferred embodiments, an absolute core pressure drop is also measured. As shown in FIG. 3, in preferred embodiments the coreflood inlet end-piece (330) is further equipped with a core inlet pressure port, as shown by element (115) in FIGS. 2A through 2D which is separated by at least one separating member which isolates the a core inlet pressure port (115) from the first phase inlet port (105) and the second phase inlet port (110). In this manner, an overall differential pressure across the core holder (310) may be measured independent of the first phase inlet pressure and the second phase inlet pressure. This overall differential pressure across the core holder (310) is facilitated by fluidly connecting the core inlet pressure port (115) and a core outlet pressure port (350) to a core differential pressure gauge or pressure measurement device (352) to measure the differential pressure. Preferably, the core outlet pressure port (350) is fabricated in the coreflood outlet end-piece (355).

In FIG. 3, also shown is a preferred embodiment wherein a screen (360) is placed between the outlet end of the core (305) and the coreflood outlet end-piece (355). This screen will help with flow distribution as well as contain particulate matter that may dislodge from the core (305). The coreflood outlet end-piece (355) also contains an outlet port (362) from which the coreflood outlet stream (364) may be discharged. In a preferred embodiment, a backpressure regulator (365) is utilized to maintain a desired pore pressure at the outlet of the portion of the core holder (310) containing the core (305). This can be adjusted in conjunction with the pressure from the overburden pump (327) to provide a desired net confining stress (difference of overburden pressure and pore pressure) on the core sample.

Coreflood Inlet End-Piece Designs Screening

Figure 4:
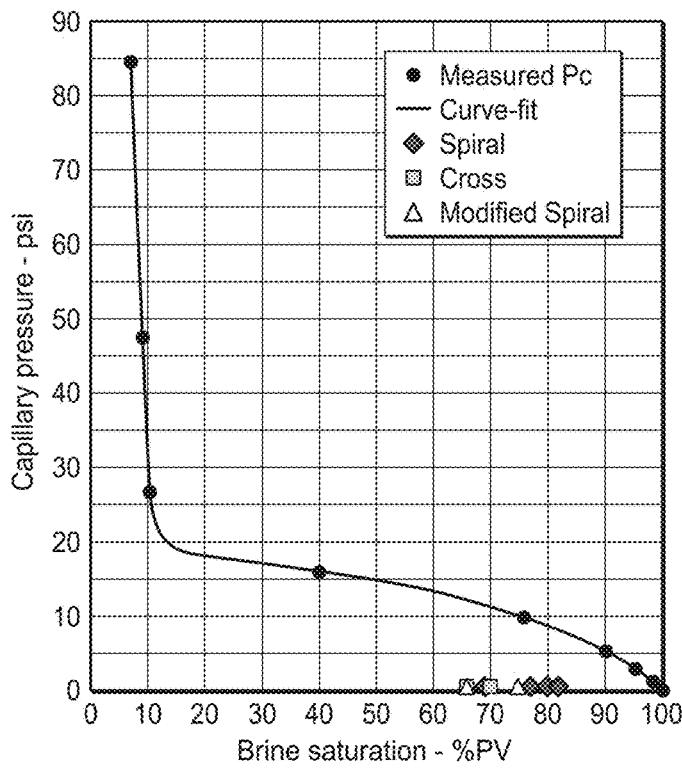
FIG. 4 shows a comparison of capillary pressure centrifuge data compared to the difference of inlet phase pressures with saturation at tested fractional flow points for the coreflood inlet end-pieces of the prior art.

The existing technology of inlet end piece designs for a core holder involves having different pattern on a metal or alloy. The examples of such conventional coreflood inlet end-pieces are shown in FIG. 1. However, due to differences in material properties of a core and a metal, it is challenging to obtain a good seal between a metal based inlet end piece and a core, and consequently, making it challenging to preventing phase mixing at inlet end piece and core junction. The small scale irregularity on a rock surface and smooth metal pattern on inlet end pieces seals imperfectly and results in mixing of injection phases and pressure equilibration between them. The challenge of obtaining good seal and resultant phase isolation exists even for metal based inlet end piece patterns where the flow paths of the injection phases do not intersect (see FIG. 1A and FIG. 1B). To demonstrate this challenge, a steady-state coreflood test on a limestone core sample (7-9 mD) using helium gas and brine (20000 ppm) as the two phase streams was performed at room temperature and 1500 psi pore pressure (2400 psi net confining stress) using metal inlet end pieces as shown in FIG. 1. Using a similar limestone core sample, the capillary pressure (difference of gas phase stream to water phase stream at different water saturation) was measured using centrifuge method at the same net confining stress and temperature. The new coreflood testing system described herein, and as shown in FIG. 3, was used to perform these lab experiments. The steady-steady coreflood was performed at multiple gas-water fractional flows (ratio of injection rate of one phase to total injection rate). At each fractional flow, a steady-state condition was obtained for pressure drop change across core and core water saturation before moving to the next fractional flow step. The pressure and saturation values were recorded at steady-state for each fractional flow point. FIG. 4 shows a comparison of the centrifuge data to the difference of inlet phase pressures with saturation at tested fractional flow points. Clearly, metal based inlet end pieces showed no phase pressure difference (as shown by capillary pressure $\Delta P$ values of zero) at the inlet at steady-state conditions, clearly indicating that phase mixing occurred at the inject face of the core. The same results were observed when a screen was located between the metal based inlet end pieces and the core.

The designs and systems disclosed herein involve a new concept of coreflood inlet end-piece designs (as well as additional associated system designs herein to take advantage of the data/information that is enabled through the use of these new coreflood inlet end-piece designs) that can prevent phase mixing at the core inlet. In an embodiment of the proposed design, both metal and an elastomer are used. The metal is used to provide: 1) a desired pattern to spread the fluid on the end piece face before entering the core, and 2) a rigid base for elastomer pattern to maintain structural integrity at high pressures. The elastomer in the design is used to provide good seal between inlet end piece and core surface to prevent phase mixing. The selected elastomers and metal/alloy needs to withstand test condition, and depending on the test conditions, the material needs to be changed. Similarly, depending on the test type, the pattern on metal and elastomer can vary. Examples of some novel coreflood inlet end piece designs of the present disclosure are shown in FIGS. 2A through 2D and have been described in detail above.

Figure 5:
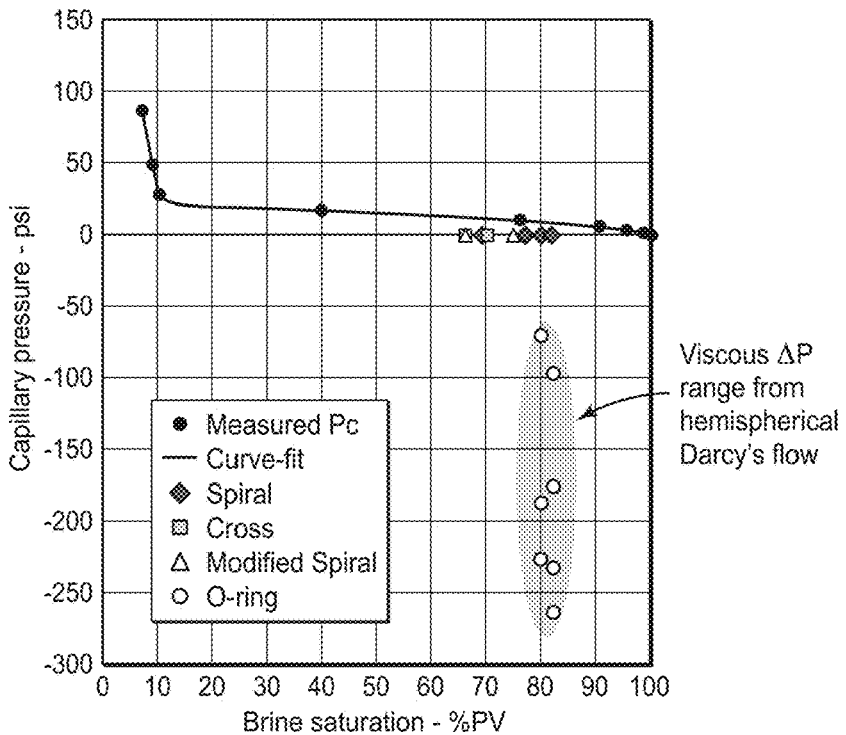
FIG. 5 shows the results of pressure difference of inlet phases with the o-ring design coreflood inlet end-piece of FIG. 2A and compare it with the prior art metal based designs.

Though the combination of metal and elastomer can prevent phase mixing, some designs that were tested provided better performance than others. For example, designs with small flow apertures like the o-ring design (FIG. 2A) provided an excellent seal between the inlet end piece and core face, but it also add significant viscous pressure contribution to the inlet phase pressure. This additional viscous pressure contribution can overwhelm capillary pressures. The additional viscous pressure contribution comes from expansion of the injection fluid envelop inside the core near inlet. This concept is demonstrated through the same experiment performed on a similar limestone core sample. FIG. 5 shows the results of pressure difference of inlet phases with the o-ring design of FIG. 2A and compares it with conventional metal based inlet end-piece designs. In this test, steady-state was obtained at multiple total flow rates for two helium fraction flows (fraction of 0.5 and 0.8). The pressure difference of helium and brine were non-zero, clearly indicating that the o-ring end piece of FIG. 2A provided a good isolating seal. However, helium-brine pressure difference at the coreflood inlet end-piece had the opposite trend than expected, with large negative magnitude as compared to centrifuge capillary pressure (see FIG. 5). The opposite trend was caused by the additional viscous pressure contribution from the o-ring design's small inlet aperture. In the o-ring design, the flow expanded in a hemispherical pattern inside the core at the two phase inlet ports. Since brine viscosity is almost two orders higher than helium viscosity, the viscous pressure drop near the brine end piece port is significant compared to the helium port, thus difference in helium-brine inlet pressure reflects as negative capillary pressure in FIG. 5. Typical measurement techniques for capillary pressure are performed in static condition with negligible viscous pressure gradients in the system. In this test, the range of measured phase pressure difference matches closely with Darcy's equation calculations for hemispherical flow in porous media. Hence, it is desirable, in preferred embodiments, to have an elastomer based inlet end piece with wider flow aperture to reduce viscous pressure contribution in measured inlet phase pressure. Use of a compatible elastomer material based on the testing conditions is important. Some elastomer may perform fine at room condition, but may lose structural integrity in presence of hydrocarbon at high pressure and temperature.

Inlet end-pieces patterns with metal and elastomer-based face design (e.g., design embodiments as illustrated in FIGS. 2C and 2D) tended to perform better than those with 100% elastomer based face design (e.g., the design embodiment as illustrated in FIG. 2B). In a 100% elastomer based design (such as illustrated in FIG. 2B), if grooves are not sufficiently deep or wide, there is a risk of pattern distortion under high pressure. For the similar test with a limestone core sample at 1500 psi pore pressure and 2400 psi net confining stress, the elastomer spiral face coreflood inlet end-piece design of FIG. 2B was able to isolate phases at the inlet for the first 4000 minutes, and later inlet phase pressure difference snapped to zero due to phase mixing. FIGS. 6A and 6B show the post-test pictures of the elastomer spiral face coreflood inlet end-piece (FIG. 6A) and the inlet face of the core sample (FIG. 6B). The salt residue from brine spreading over most of the inlet end piece face (FIG. 6A) and the brine streak connecting positions of injection ports for both phases on the core face (FIG. 6B) provide clear evidence of brine mixing in the test. It is believed that the risk is losing structural integrity under high pressures can be reduced if, for the inlet end-piece face design, the end-piece is comprised of both an elastomer and metal.

Preferred embodiments of the coreflood inlet end-piece designs here may (optionally) comprise of: 1) a combination of both metal and elastomer, 2) wider aperture or surface area of injection phases to minimize viscous pressure contribution in measured inlet phase pressures, 3) an elastomer material which is compatible with the mechanical and/or process conditions, 4) face design consisting of both metal and elastomer, or 100% elastomer with sufficient groove width and depth, and/or 5) face design consisting of both metal and elastomer, wherein the ratio of the elastomer surface area-to-overall face surface area is minimized to increase sealing pressure and maximize injection phase injection cross section. Illustrative examples of embodiments comprising at least one of these optional preferred features are shown in the designs of FIGS. 2A through 2D.

For the similar experiment on a limestone core sample, the "half-moons" coreflood inlet end piece (as illustrated in FIG. 2D) successfully isolated both brine and helium phases. FIG. 7 shows the difference of phase pressures at steady-state condition for multiple fraction flow and multiple rates at each fractional flow. Clearly, the difference of phase pressures at the inlet is non-zero, indicating successful isolation of injection phases at the face of the inlet end piece. Further, the difference of phase pressures at the inlet is positive, indicating lower viscous contribution in the measurements because of better phase spreading on the end piece face (or wide injection cross section) compared to an end piece with small injection aperture such as the coreflood inlet end-piece design shown in FIG. 2A. Though viscous contributions in the difference in inlet phase pressures are small with the half-moons design, they are not zero. The non-zero viscous contribution in the inlet phase pressures cause a flow rate dependence in the difference between inlet phase pressures. Because of the viscous gradient effects, the difference in inlet phase pressures (shown in FIG. 7 by the open circles) is lower than measured under static capillary pressure using the centrifuge method in FIG. 7 (as shown by the solid curve). Thus, the viscous contribution has to be subtracted from the difference in inlet phase pressures to yield capillary pressure from a steady-state coreflood test.

As such, by utilizing the novel coreflood inlet end-piece designs and the associated coreflood testing systems as illustrated in this disclosure, the capillary pressure ($P_c$), which is typically used in the industry and is measured by such existing industry tests as the centrifugal method as we described herein, can be determined through the use of this simple test by measuring the separate phase pressure data as disclosed at multiple flow points (dynamic data points) and then mathematically determining the capillary pressure by eliminating the viscous effects. The procedure for doing this is described further as follows.

Viscous Pressure Correction

This section describes how to take the separate phase pressure data as disclosed at multiple flow points (dynamic data points) from the coreflood testing apparatus and methods as disclosed herein and calculate the capillary pressure ($P_c$). As discussed, the difference of phase pressures at the inlet equals capillary pressure only at static condition (zero flow rate). However, in a coreflood test (both steady-state and unsteady-state tests), one or both phases are continuously injected, and the phase pressures at the inlet have both capillary and viscous pressure contributions. Hence, a method is required to subtract-out the viscous pressure contribution from the difference of phase pressures at the inlet taken by this apparatus and methods.

Figure 8:
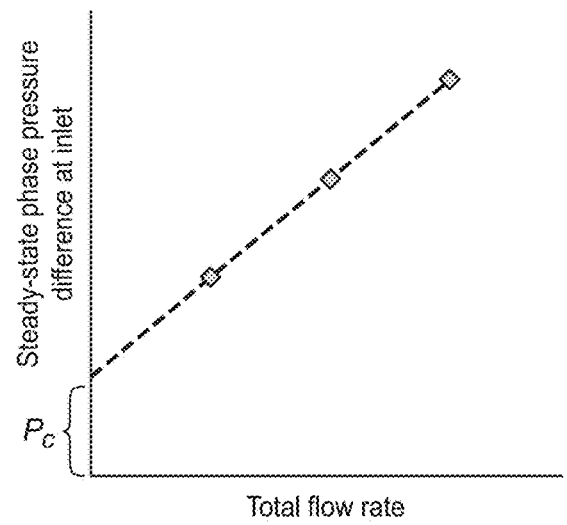
FIG. 8 illustrates that for a given fractional flow, capillary pressure (Pc) is equal to the intercept of the trend line for the plot of steady-state phase pressure difference at inlet with total flow rate.

In a steady-state coreflood test, viscous pressure contributions can be corrected by performing tests at multiple flow rates for each fractional flow. Here, steady-state is achieved at multiple flow rates, and flow and pressure measurements are taken with the apparatus. As shown in FIG. 8, for a given fractional flow, capillary pressure ($P_c$) is equal to the intercept of the trend line for the plot of steady-state phase pressure difference at the inlet with total flow rate (FIG. 8). Close to the inlet, fluid saturation does not change significantly with flow rates. Hence, the phase pressure difference at the inlet changes substantially linearly with total flow rate for a typical test steady-state test, and the intercept of the linear trend equals capillary pressure. The capillary pressure measured using the above method corresponds to capillary end-effect corrected fluid saturation, which can be estimated using the Intercept Method, any best fit curve model, or through in-situ saturation monitoring. In tests with sufficiently high pressure drop across the core, the saturation correction might be small and within experimental accuracy, and average saturation across the core may be used. Multiple points on the capillary pressure curve are obtained by performing a test with multiple fraction flow points. At each fractional flow point, a steady-state condition is obtained at several total flow rates. The total flow rates are always increased for a given fractional flow to avoid a hysteresis effect. Similarly, the fractional flow points in a test are changed either in an increasing or decreasing fashion (depending on imbibition or drainage cycles) to avoid hysteresis effect.

Example of Application of System and Methods at Reservoir Condition

A water-oil steady-state coreflood test was performed to demonstrate the concept of obtaining capillary pressure from the difference of phase pressures at the coreflood inlet, post viscous pressure correction, using the new coreflood inlet end-piece designs, associated coreflood testing system designs, and associated methods.

Figure 9:
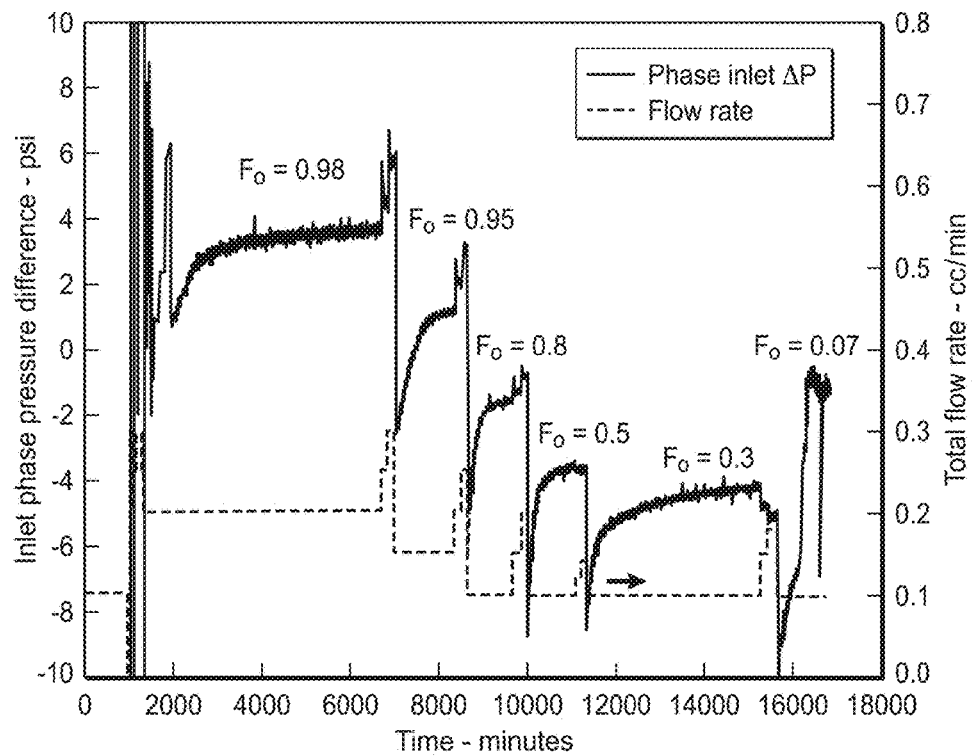
FIG. 9 shows the phase pressure difference (oil minus water phase pressure) at the inlet and total flow rate with time as taken during the test of the coreflood system with a half-moons coreflood inlet end-piece (as shown in FIG. 2D).

This test was performed on preserved (native condition) core plugs stacked in series to make a 10 inches long core composite. The test was performed at reservoir temperature, pore and overburden pressures using live fluids (gas dissolved in oil and brine to replicate reservoir fluid condition). The viscosities of oil and water in this example were similar. The test was performed on an apparatus with configuration similar to FIG. 3 utilizing a half-moons coreflood inlet end-piece as shown in FIG. 2D. The test was an imbibition steady-state test, where both oil and water were co-injected at increasing water fractional flow steps in the oil saturated composite at residual (immobile) water saturation. At each fractional flow point, steady-state condition was obtained at multiple total flow rates, where total flow rates were increased in steps to avoid hysteresis effect. The total flow rate was reduced concurrently with fractional flow change (as shown in FIG. 9). Since the saturation change is significant between two consecutive fractional flows, reducing total flow rate between consequent fractional flows imposes minimal hysteresis.

FIG. 9 shows the phase pressure difference (oil minus water phase pressure) at the inlet and total flow rate with time as taken during the test. As discussed prior, the drop in total flow rate correspondingly signifies change in fraction flow in this test since the oil phase flow was held constant. The term "$F_o$" as shown in FIG. 9 is the "oil fractional flow" which is equal to the oil phase flow rate divided by the total flow rate (oil plus water) during the test.

As can be seen in FIG. 9, the difference in phase pressure at the inlet is non-zero and ranged from −10 to +10 psi. Hence, it is clearly shown that the half-moons coreflood inlet end-piece utilized in this test was able to prevent phase mixing at the interface between the coreflood inlet end piece face and the core face.

Figure 10A:
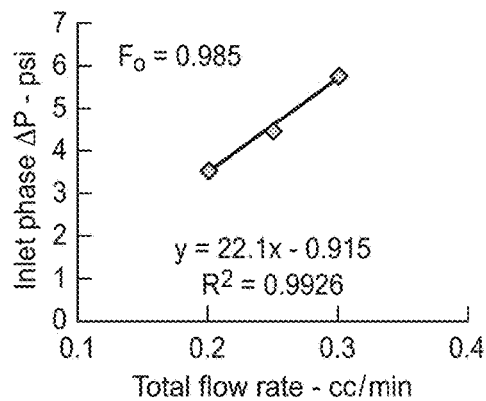
FIGS. 10A through 10C show the plots of oil phase pressure minus the water phase pressure at the coreflood inlet end-piece at steady-state condition with total flow rate at oil fractional flows of 0.985, 0.9 and 0.3, respectively as obtained during testing of the coreflood system with a half-moons coreflood inlet end-piece (as shown in FIG. 2D).
Figure 10B:
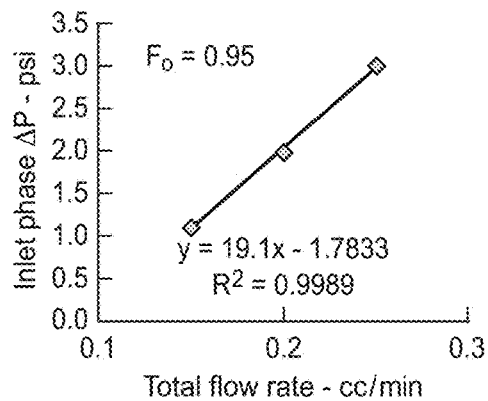
Figure 10C:
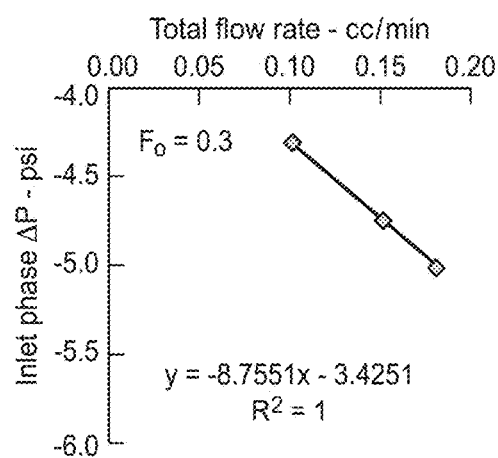

In theory, the capillary pressure contribution of the measured phase pressures does not change with flow rate. In FIG. 9, the phase pressure difference at the inlet is found to change with increase in flow rate at each fraction flow, indicating viscous effects in the measurements. FIGS. 10A through 10C show the plots of oil phase pressure minus the water phase pressure at the coreflood inlet end-piece at steady-state condition with total flow rate at oil fractional flows of 0.985, 0.9 and 0.3, respectively. All three plots show a substantially linear trend. Similar linear trends were observed with other fractional flow points (not shown). Because of the relative viscous flow effects between the two phases, the linear trend has a positive slope for oil fractional flow above 0.5 and a negative slope below 0.5. Since oil and water have similar viscosity in this test, the phase with higher flow rate will have the greatest effect on the viscous pressure contribution at the inlet. Hence, above 0.5 fractional flows, the oil phase had a higher viscous pressure contribution included in the inlet oil phase pressure measurement compared to the water phase, which caused the positive slope on the plot, and vice versa.

Figure 11:
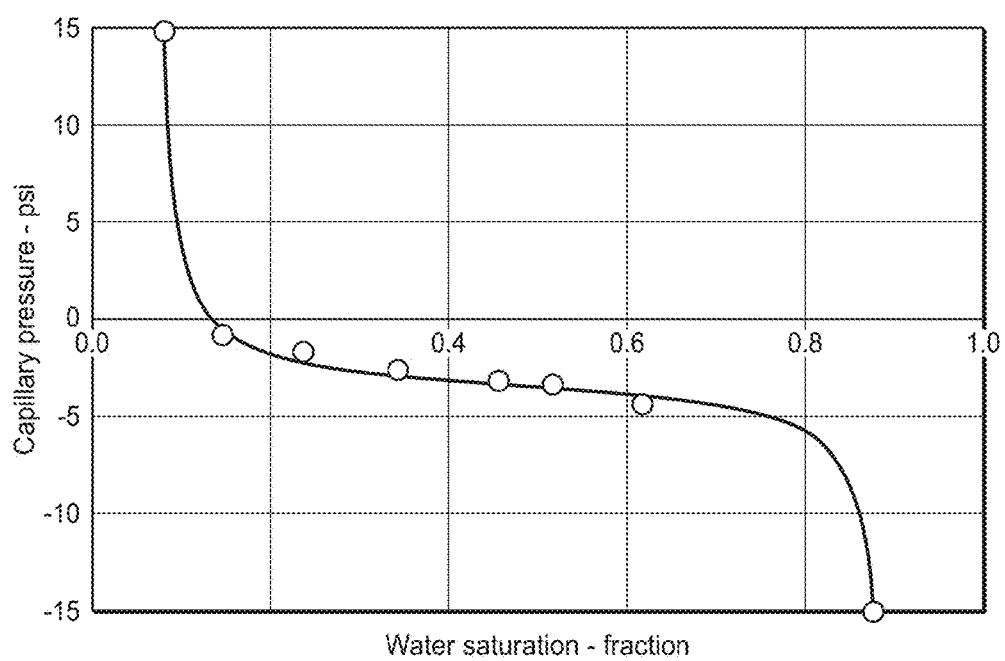
FIG. 11 shows the calculated capillary pressure ($P_c$) plot derived from the test data from and intercept calculations described herein.

A capillary pressure curve for this test was made, utilizing the intercepts of the plots of oil minus water phase inlet pressures with total flow rate for each fractional flow, and its corresponding water saturation is shown in FIG. 11. The water saturation was calculated after applying the Intercept Method. Since pressure drop in this test was high, the capillary end-effect correction to water saturation was small. FIG. 11 shows the calculated capillary pressure ($P_c$) plot for this test. The saturation at the first and last point represents residual oil and residual water saturation for this test. In theory, capillary pressure curves asymptote at residual saturations at both ends, but values of 15 psi and −15 psi were used to denote the capillary pressures at residual saturations. This plot closely matched the centrifuge capillary pressure curve of the similar lithology run by the standard centrifuge capillary pressure method.

As can be seen by the tests herein, the novel coreflood inlet end-pieces, coreflood testing systems, and modified coreflood testing methods and associated analyses described herein successfully isolated the phases in a coreflood test allowing discrete inlet phase pressure measurements. Further, the inlet phase pressure at steady-state condition can be used to estimate capillary pressure of the core after applying viscous pressure correction. With the systems disclosed herein, both positive and negative values (forced and spontaneous) of a capillary pressure curve can be captured (see FIG. 11, where the data plotted from the testing utilizing the systems herein contains both positive and negative capillary pressure values). This is an improvement over other methods like the centrifuge method which cannot capture the spontaneous imbibition or spontaneous drainage portions of a capillary pressure curve, and only captures forced imbibition or forced drainage. If both imbibition and drainage cycles are performed in a steady-state test, for example, water saturation increased in oil filled core (imbibition) and later oil saturation increased towards the initial condition, then both imbibition and drainage cycles capillary pressure can be obtained.

Wettability Measurements

Wettability of the core can be also be obtained via the apparatus, systems and methods herein by utilizing the imbibition and drainage capillary pressure curves generated from the present coreflood testing systems and methods herein and using either Amott-Harvey (or Amott) or USBM (US Bureau of Mines) wettability index method to calculate the wettability of the core sample. This is another unique feature of the present designs and methods herein.

Thus, using invented inlet end piece designs, coreflood testing systems, and the test methodologies discussed herein, all three (3) critical core property measurements of relative permeability, capillary pressure and wettability can be obtained through simultaneous measurements in a single steady-state test, which may result in significant time and cost saving, and help eliminate errors that can be introduced in the prior art in utilizing separate core plugs for each of these different three (3) tests.

Embodiments

A non-limiting list of embodiments of the present invention as follows:

Embodiment 1. An inlet end-piece for a coreflood testing system, comprising:
a first surface;
a first phase inlet port substantially located at the first surface; and
a second phase inlet port substantially located at the first surface;
wherein substantially within the plane of the first surface, the first phase inlet port and the second phase inlet port are separated by at least one isolation member.

Embodiment 2. The inlet end-piece of Embodiment 1, wherein the at least one isolation member is made of an elastomer.

Embodiment 3. The inlet end-piece of Embodiment 1, wherein substantially within the plane of the first surface, the first phase inlet port and the second phase inlet port are fluidly isolated by at least two isolation members.

Embodiment 4. The inlet end-piece of Embodiment 1, further comprising a core inlet pressure port substantially located at the first surface.

Embodiment 5. The inlet end-piece of Embodiment 4, wherein the isolation member is fabricated from a single piece and comprises a separate sealing area for each the first phase inlet port, the second phase inlet port, and the core inlet pressure port, and wherein the separate sealing areas are fabricated into a face of the isolation member.

Embodiment 6. The inlet end-piece of Embodiment 5, wherein the separate sealing areas for each the first phase inlet port and the second phase inlet port are formed by grooves in the isolation member.

Embodiment 7. The inlet end-piece of Embodiment 5, wherein the separate sealing areas for each the first phase inlet port and the second phase inlet port are formed by voids fabricated through the isolation member.

Embodiment 8. The inlet end-piece of Embodiment 3, wherein each of the isolation members are substantially circular or semi-circular in shape.

Embodiment 9. The inlet end-piece of Embodiment 8, wherein in the plane of the first surface, the area within the boundaries of each of the isolation members is at least 25% of the total area of the first surface.

Embodiment 10. The inlet end-piece of Embodiment 8, wherein grooves are fabricated in the first surface within the boundaries of at least one of the isolation members.

Embodiment 11. The inlet end-piece of Embodiment 1, further comprising:
a third phase inlet port substantially located at the first surface;
wherein substantially within the plane of the first surface, the first phase inlet port, the second phase inlet port and the third phase inlet port are each separated by at least one isolation member.

Embodiment 12. A coreflood testing system comprising:
a coreholder which comprises:
a cavity;
a core sample placed with the cavity;
an inlet end-piece at a first end of the cavity; and
an outlet end-piece at a second end of the cavity, wherein the second end of the cavity is opposite of the first end of the cavity;
wherein the inlet end-piece comprises:
a first surface;
a first phase inlet port substantially located at the first surface; and
a second phase inlet port substantially located at the first surface;
wherein substantially within the plane of the first surface, the first phase inlet port and the second phase inlet port are separated by at least one isolation member; and
wherein the isolation member is in contact with the first surface and a first end of the core sample, and creates a seal that fluidly isolates the first phase inlet port from the second phase inlet port substantially within the plane of the first surface.

Embodiment 13. The coreflood testing system of Embodiment 12, further comprising:
a first pressure measurement device fluidly connected to the first phase inlet port and a second pressure measurement device fluidly connected to the second phase inlet port; or
a differential pressure measurement device fluidly connected to both the first phase inlet port and the second phase inlet port.

Embodiment 14. The coreflood testing system of Embodiment 13, wherein the inlet end-piece further comprises a core inlet pressure port located at the first surface; and the first phase inlet port, the second phase inlet port, and the core inlet pressure port are each separated from each other substantially within the plane of the first surface by the at least one isolation member.

Embodiment 15. The coreflood testing system of Embodiment 14, wherein the outlet end-piece comprises a core outlet pressure port; and the core inlet pressure port and the core outlet pressure port are fluidly connected to a differential pressure measurement device.

Embodiment 16. The coreflood testing system of Embodiment 12, wherein at least one isolation members comprises a first phase inlet port isolation member and a second phase inlet port isolation member; wherein substantially within the plane of the first surface, the first phase inlet port is located within the boundary of the first phase inlet port isolation member, and the second phase inlet port is located within the boundary of the second phase inlet port isolation member.

Embodiment 17. The coreflood testing system of Embodiment 16, wherein the first phase inlet port isolation member and the second phase inlet port isolation member are substantially circular or semi-circular in shape.

Embodiment 18. The coreflood testing system of Embodiment 17, wherein substantially within the plane of the first surface, the area within the boundaries of each the first phase inlet port isolation member and the second phase inlet port isolation member are at least 25% of the total area of the first surface.

Embodiment 19. The coreflood testing system of Embodiment 18, wherein grooves are fabricated in the first surface, within the boundaries of each of the isolation members.

Embodiment 20. The coreflood testing system of Embodiment 12, wherein the isolation member is fabricated from a single piece and comprises a separate sealing area for each the first phase inlet port, the second phase inlet port, and the core inlet pressure port; and wherein the separate sealing areas are fabricated into a face of the isolation member.

Embodiment 21. The coreflood testing system of Embodiment 20, wherein the separate sealing areas for each the first phase inlet port and the second phase inlet port are formed by grooves in the isolation member.

Embodiment 22. The coreflood testing system of Embodiment 20, wherein the separate sealing areas for each the first phase inlet port and the second phase inlet port are formed by voids fabricated through the isolation member.

Embodiment 23. The coreflood testing system of Embodiment 13, wherein the core sample and the cavity of the coreholder are substantially cylindrical in shape, and further comprising:
an overburden sleeve; and
an overburden pump;
wherein the overburden sleeve surrounds an outside circumference of the core sample and fluidly separates the core sample from an interior circumference of the cavity of the coreholder; and an outlet of the overburden pump is fluidly connected to an annulus between the overburden sleeve and the interior circumference of the cavity of the coreholder.

Embodiment 24. The coreflood testing system of Embodiment 12, further comprising:
a third phase inlet port substantially located at the first surface;
wherein substantially within the plane of the first surface, the first phase inlet port, the second phase inlet port and the third phase inlet port are separated by at least one isolation member; and
wherein the isolation member is in contact with the first surface and a first end of the core sample, and creates a seal substantially within the plane of the first surface that fluidly isolates the first phase inlet port, the second phase inlet port, and the third phase inlet port from one another.

Embodiment 25. A coreflood testing process, comprising:
flowing a first phase fluid through a first phase fluid inlet of an inlet end-piece of a coreholder and into a first inlet face of a core sample, wherein the core sample is located within a cavity of the coreholder; and
flowing a second phase fluid through a second phase fluid inlet of the inlet end-piece to the coreholder and into the first inlet face of the core sample;
wherein substantially with in the plane of the first inlet face of the core sample, the first phase fluid is fluidly isolated from the second phase fluid by at least one isolation member.

Embodiment 26. The coreflood testing process of Embodiment 25, wherein:
the first phase fluid inlet is substantially located at a first surface of the inlet end-piece; and
the second phase fluid inlet is substantially located at the first surface of the inlet end-piece;
wherein substantially within the plane of the first inlet face of the core sample, the first phase inlet port and the second phase inlet port are fluidly isolated by the at least one isolation member.

Embodiment 27. The coreflood testing process of Embodiment 25, wherein the at least one isolation member is made of an elastomer.

Embodiment 28. The coreflood testing process of Embodiment 25, further comprising:
measuring a first pressure of the first phase fluid near the first inlet face of the core sample and measuring a second pressure of the second phase fluid near the first inlet face of the core sample; or
measuring a differential pressure between the first pressure of the first phase fluid near the first inlet face of the core sample and the first pressure of the second phase fluid near the first inlet face of the core sample.

Embodiment 29. The coreflood testing process of Embodiment 28, further comprising:
flowing the first phase fluid and the second phase fluid from the first inlet face of the core sample through the core sample to a first outlet face of the core sample;
measuring the flowrate of the first phase fluid; and
measuring the flowrate of the second phase fluid.

Embodiment 30. The coreflood testing process of Embodiment 29, further comprising:
a core inlet pressure port fluidly connected to the core sample through the inlet end-piece;
wherein substantially within the plane of the first inlet face of the core sample, the first phase fluid, the second phase fluid, and the inlet core pressure port are each fluidly isolated by the at least one isolation member.

Embodiment 31. The coreflood testing process of Embodiment 30, further comprising:
detecting an inlet core pressure at the first inlet face of the core sample through the inlet core pressure port;
wherein the inlet core pressure is independent of the pressure of either the first phase fluid or the pressure of the second phase fluid at the face of the core sample.

Embodiment 32. The coreflood testing process of Embodiment 29, further comprising:
determining a relative permeability and a capillary pressure of the core sample from the measurements obtained from a single coreflood test.

Embodiment 33. The coreflood testing process of Embodiment 32, wherein the single coreflood test comprises taking measurements at multiple flowrates of the first phase fluid, multiple flowrates of the second phase fluid, or both.

Embodiment 34. The coreflood testing process of Embodiment 32, further comprising:
determining a wettability of the core sample from the measurements obtained from the single coreflood test.

Embodiment 35. The coreflood testing process of Embodiment 32, wherein the first phase fluid comprises oil and the second phase fluid comprises water or gas.

Embodiment 36. The coreflood testing process of Embodiment 25, further comprising:
a) taking a first set of measurements at a first flowrate of the first phase fluid and a first flowrate of the second phase fluid at a first oil fractional flowrate;

b) taking a second set of measurements at a second flowrate of the first phase fluid and a second flowrate of the second phase fluid at a second oil fractional flowrate, wherein the first oil fractional flowrate and the second oil fractional flowrate are substantially the same;

c) determining a first differential pressure between the pressure of the first phase fluid and the pressure of the second phase fluid at the face of the core sample based on the first set of measurements;

d) determining a second differential pressure between the pressure of the first phase fluid and the pressure of the second phase fluid at the face of the core sample based on the second set of measurements;

e) determining a first total flow rate which is the sum of the first flowrate of the first phase fluid and first flowrate of the second phase fluid;

f) determining a second total flow rate which is the sum of the second flowrate of the first phase fluid and second flowrate of the second phase fluid; and g) determining the capillary pressure by finding the pressure differential intercept at zero total flow of the first phase fluid and the second phase fluid.

Embodiment 37. The coreflood testing process of Embodiment 36, wherein the first set of measurements and the second set of measurements are taken at substantially steady state conditions.

Embodiment 38. The coreflood testing process of Embodiment 36, further comprising:

performing steps a)-g) at least 2 times wherein in each set of steps, the first fractional flowrate and the second fractional flowrate are substantially the same in the step, but are different than the first fractional flowrate and the second fractional flowrate used in a prior set of steps; and determining a capillary pressure curve from the capillary pressures determined from each set of steps.

Embodiment 39. The coreflood testing process of Embodiment 38, wherein steps a)-g) are performed at least 5 times.

Embodiment 40. The coreflood testing process of Embodiment 39, wherein the capillary pressure curve comprises both positive and negative capillary pressure values.

Embodiment 41. The coreflood testing process of Embodiment 36, wherein the core sample and the cavity of the coreholder are substantially cylindrical in shape, and further comprising:
  an overburden sleeve; and
  an overburden pump;
  wherein:

the overburden sleeve surrounds an outside circumference of the core sample and fluidly separates the core sample from an interior circumference of the cavity of the coreholder;

an outlet of the overburden pump is fluidly connected to an annulus between the overburden sleeve and the interior circumference of the cavity of the coreholder; and the overburden pump supplies an overburden pressure fluid to the annulus at a pressure higher than a pressure of the first phase fluid and higher than the pressure of the second phase fluid.

Embodiment 42. The coreflood testing process of Embodiment 25, further comprising:

flowing a third phase fluid through a second phase fluid inlet of the inlet end-piece to the coreholder and into the first inlet face of the core sample;

wherein substantially with in the plane of the first inlet face of the core sample, the first phase fluid, the second phase fluid, and the third phase fluid are fluidly isolated from one another by at least one isolation member.

What is claimed is:

1. An inlet end-piece for a coreflood testing system, comprising:
  a first surface;
  a first phase inlet port substantially located at the first surface; and
  a second phase inlet port substantially located at the first surface;
  wherein substantially within a plane of the first surface;
  wherein substantially within the plane of the first surface, the first phase inlet port and the second phase inlet port are fluidly isolated by at least two isolation members;
  wherein each of the isolation members are substantially circular or semi-circular in shape; and
  wherein grooves are fabricated in the first surface within the boundaries of at least one of the isolation members.

2. The inlet end-piece of claim 1, further comprising a core inlet pressure port substantially located at the first surface.

3. The inlet end-piece of claim 1, further comprising:
  a third phase inlet port substantially located at the first surface;
  wherein substantially within the plane of the first surface, the first phase inlet port and the second phase inlet port are separated from the third phase inlet port by at least one additional isolation member.

* * * * *